United States Patent [19]

Masuda

[11] Patent Number: 4,769,609
[45] Date of Patent: Sep. 6, 1988

[54] MEASUREMENT OF ULTRA-FINE PARTICLES UTILIZING PULSED CORONA SIGNALS

[76] Inventor: Senichi Masuda, 3-2-1-415 Nishigahara, Kita-ku, Tokyo, Japan

[21] Appl. No.: 909,909

[22] Filed: Sep. 19, 1986

[51] Int. Cl.⁴ .............................. G01N 27/62
[52] U.S. Cl. .................... 324/455; 324/71.4; 324/464; 340/627; 73/865.5; 356/313
[58] Field of Search .............. 55/270; 73/28, 865.5; 324/455, 464, 465, 466, 470, 71.4; 340/632, 627; 356/311, 313; 364/555

[56] References Cited

U.S. PATENT DOCUMENTS

| | | | |
|---|---|---|---|
| 3,526,828 | 9/1970 | Whitby | 324/464 |
| 3,718,029 | 2/1973 | Gourdine et al. | 73/28 |
| 3,787,123 | 1/1974 | Sigrist | 73/28 X |
| 4,198,160 | 4/1980 | Kachel et al. | 324/71.4 X |
| 4,312,180 | 1/1982 | Reif et al. | 73/28 X |
| 4,531,402 | 7/1985 | Reif et al. | 73/28 |

*Primary Examiner*—A. D. Pellinen
*Assistant Examiner*—H. L. Williams
*Attorney, Agent, or Firm*—Koda and Androlia

[57] ABSTRACT

In the known electrical mobility analyzer, a novel means for charged particle detection instead of measuring the low level current carried by the particles is provided. This detection is based on the burst corona occuring from a positive corona electrode applied with a voltage slightly lower than its onset voltage at an instant when a negatively charged particle arrives at the tip of the corona electrode. This detection detects and counts the burst corona pulses produced by the particles negatively precharged.

3 Claims, 2 Drawing Sheets

MEASUREMENT OF ULTRA-FINE PARTICLES UTILIZING PULSED CORONA SIGNALS

BACKGROUND OF THE INVENTION

1. Field of the Invention

This invention provides an instrument for measuring the number concentration and particle size distribution of ultra-fine particles with less than 0.1 micrometer diameter suspended in gas.

2. Prior Art

The conventional instrument for measuring gas-laden particles with the same extremely small size is the "electrical mobility analyzer" in which the particles are precharged and pass through a DC electric field for separation of charged particles according to their electrical mobility. The detection of the particles in this type of instrument is made by measuring the very low DC current carried by the separated charged particles.

In the conventional instrument described above, the level of the detected current carried by the charged particles becomes so small, when the particle size is extremely small, say less than 0.1 micrometer, and its number concentration is very low, that its measuring error becomes excessively large, finally to make a reliable measurement impossible.

SUMMARY OF THE INVENTION

This invention uses, in the known electrical mobility analyzer, a novel means of charged particle detection instead of measuring the low level current carried by the particles. This detection means is based on the burst corona occurring from a positive corona electrode applied with a voltage slightly lower than its onset voltage at an instant when a negatively charged particle arrives at the tip of the corona electrode. This detection means detects and counts the brust corona pulses produced by the particles negatively precharged.

In keeping with the principles of this invention, the measuring instrument has a unique combination of elements including particle precharging means having a gas intake and a gas outlet, for imparting negative charge to ultra-fine particles; a particle separating means comprising a parallel electrode system with a gas passage in its electric gap and a variable DC voltage supply for applying a variable DC voltage to two electrodes of the parallel electrode system; a carrier gas feed system for feeding clean carrier gas from one end of the parallel electrode system and passing the carrier gas through the gas passage in the electrode gap in a laminar flow to the other end of the parallel electrode system, comprising a gas intake, absolute filter, and a suction pump; a sample gas feeding means for feeding the sample gas containing the negatively charged ultra-fine particles out of the particle precharging means to the feeding position on the negative electrode of the parallel electrode system near its upstream end of the carrier gas, comprising a feed pipe and a sample gas supply port at the feed position; a probe gas suction system for extracting a part of the flow gas together with the arriving negatively charged ultra-fine particles at the extracting position on the positive electrode of the parallel electrode system near its downstream end, comprising probe gas extraction port, a gas flow path for passing the extracted probe gas and a suction pump; and a counting means of negatively charged ultra-fine particles located in the gas flow path for detecting and counting the negatively charged ultra-fine particles, which includes a corona electrode system out of a corona electrode and a counter electrode insulated therefrom, a DC voltage supply for applying a DC voltage between the corona electrode and counter electrode in a polarity so as to make the former electrode positive and a burst corona counter for detecting and counting the burst coronas occurring at the corona electrode.

DETAILED DESCRIPTION OF THE INVENTION

Figure 1:
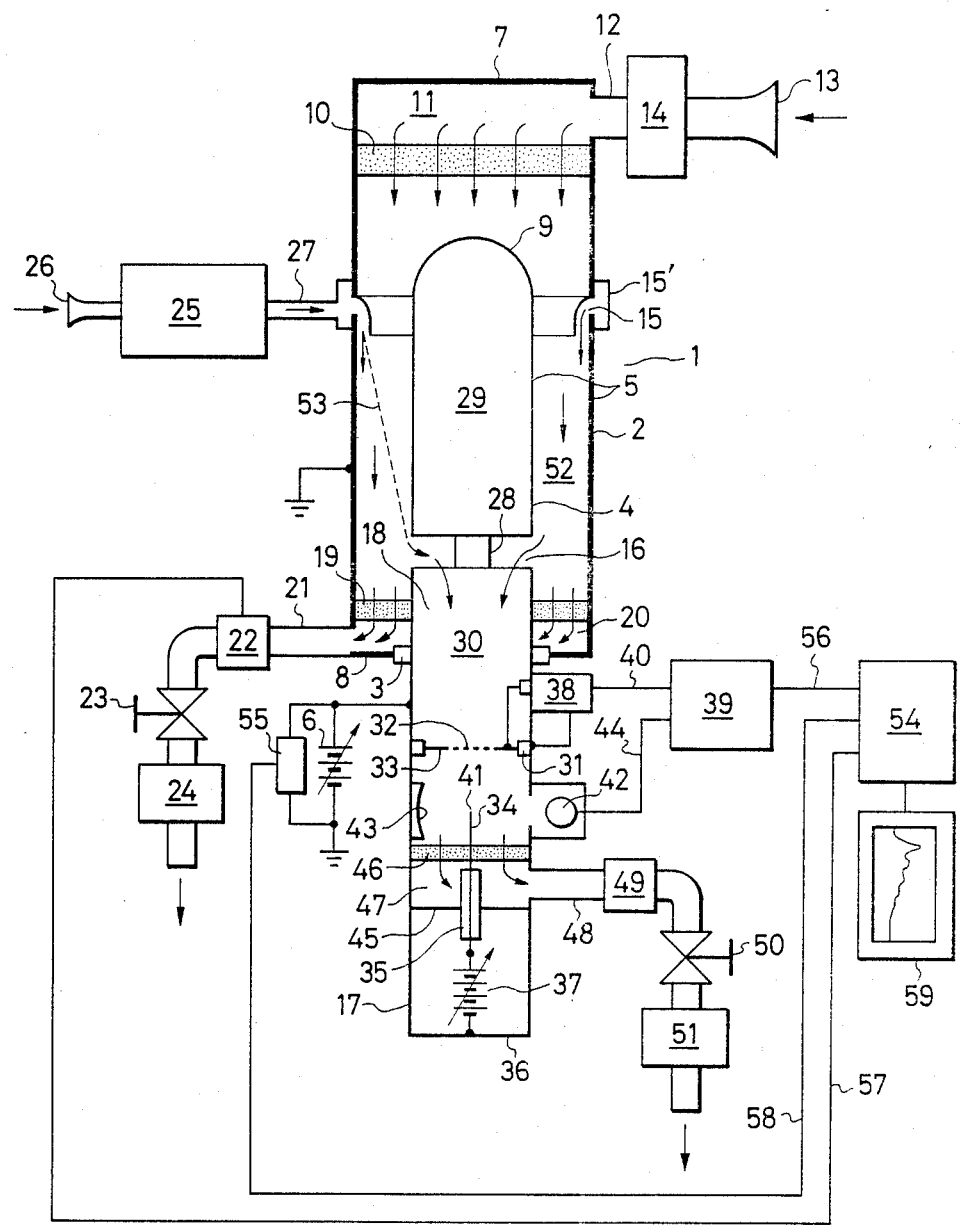
FIG. 1 illustrates an example of the embodiment of the present invention.

This invention, a "measuring instrument of ultra-fine particles", comprises a "precharging means" using negative corona discharge, radio isotope, etc. for imparting a negative elementary charge e [C] to individual particle, a "particle separating means" including a parallel electrode system in a form of concentric cylinder electrodes or parallel plane electrodes and a variable DC voltage source for applying a variable DC voltage V [V] between these two parallel electrodes, a "carrier gas feed system" for feeding clean carrier gas from one end of the parallel electrode system and passing the gas in a form of laminar flow through the gap between the two electrodes of the parallel electrode system, which includes a gas intake opening, a filter for cleaning the intaken carrier gas and a gas pump for enforcing the flow of the carrier gas, a "sample gas feeding means" for feeding the sample gas with negatively precharged ultra-fine particles from the precharging means to the inside of the parallel electrode system at a predetermined constant flow rate through a connecting pipe and a supply port of the precharged ultra-fine particles located near the upstream end of the negative electrode of the parallel electrode system, the sample gas feeding means comprising a connecting pipe between the precharging means and the parallel electrode system and the supply port, a "probe gas suction system" for extracting a part of the sample gas (probe gas) at a position close to the downstream end of the positive electrode of the parallel electrode system, together with the charged ultra-fine particles arrived at this position, the probe gas suction system comprising a probe gas extraction port located at the position for probe gas extraction, a gas flow path for passing the extracted probe gas, and a suction pump, and a "counting means of negatively charged ultra-fine particles" located in the gas flow path, the counting means comprising a corona electrode system of a corona electrode (such as a needle electrode, pipe-shaped electrode, wire electrode, knife-shaped electrode, cylinder-with-sharp edge electrode, etc.) and a counter electrode (such as plate electrode, mesh electrode, cylindrical electrode, etc.) facing thereto and insulated therefrom, a direct current voltage supply for applying a DC voltage slightly lower than the positive corona onset voltage between the corona electrode and counter electrode in the polarity so as to make the the corona electrode positive to the counter electrode, a burst corona counter for detecting and counting the burst corona occuring from the positive electrode as the concurrent pulse current flowing through the corona electrode or the concurrent light pulse.

An ultra-fine particle imparted with a negative elementary charge, e [C], in the precharging means, and fed through the sample gas feeding means and the supply port inside of the parallel electrode system of the particle separating means at the supply position on its negative electrode close to its upstream end subjects to Coulombic force to travel towards its positive electrode, with an average velocity:

$$v_e = c\overline{E}c_m/(6\pi\eta a)[m/s] \quad (1)$$

where $\overline{E} = V/d$ = average field intensity between the positive and negative electrodes [V/m], d = electrode gap [m], $\eta$ = gas viscosity [Ns/m], a = particle radius [m], $C_m$ = Cunningham's correction factor = $1 + 2.514(\lambda/a) + 0.8(\lambda/a) \exp[-0.55(2a/\lambda)]$, $\lambda$ = mean free path of gas molecules.

From Equation (1) in consideration of the Cunningham's correction factor as described above, it becomes evident that the particle drift velocity $v_e$, is a unique function of the particle radius, a, and the applied voltage V, as $$v_e = v_e(a, V) \quad (2)$$

Letting the average flow velocity of the carrier gas in the gap between the two electrodes be $v_g$ [m/s], and the length between the supply port and the extraction port be L [m], it is understood that only the particles satisfying the following condition are extracted with the probe gas from the extraction port to be led to the corona electrode system of the counting means of negatively charged ultra-fine particles.

$$\frac{L}{v_g} = \frac{d}{v_e(a,V)} \quad (3)$$

These particles arriving at the corona electrode system immediately subject to Coulombic force and reach the detecting zone in the close vicinity of the positive corona electrode tip. Under the influence of a very strong local electric field in the detecting zone, electrons are detached from individual negatively charged ultra-fine particles, including negative ions, a phenomenon called "field-detachment". An electron detached travel towards the tip of the positive corona electrode, causing "electron avalanche" through the ionization of neutral gas molecules by its collision, which produces a great number of charge carriers (electrons and positive ions) to be detected as a current pulse and a light emission. This is the "positive burst corona" occuring at a voltage level slightly below the onset of the continuous positive corona.

Hence, by counting this pulse current or the light emission for a certain period of time, or by measuring its counting rate, with the aid of the "burst corona counter", it is possible to measure the number concentration N(a) of the particles having a certain radius, a, determined by the Equation (3). Furthermore, by varying the voltage, V, it is possible to measure the size-dependent number concentration of the particles, and their particle size distribution.

When properly designed and operated, it is possible by this novel instrument to exactly measure the value of N(a) and the particle size distribution even in the case when the particle concentration is very low and the particle size is extremely small, down to the ionic size, because one single burst corona corresponds to one single particle arriving at the detecting zone.

In FIG. 1, the particle separating means 1 includes a grounded outer cylindrical electrode 2 and an inner coaxial cylindrical electrode 4 insulated therefrom with an insulator 3—both electrode constituting the parallel electrode system of coaxial cylinder configuration 5—and a DC variable voltage supply 6 which applies a variable DC voltage between the two electrodes in a polarity so as to make the inner electrode 4 positive in relation to the outer electrode 2. The outer cylindrical electrode is attached at its upper and lower ends with the covering circular discs 7 end 8. A porous disc 10 for straightening gas stream is located, in parallel to the covering disk 7, at a position between the disk 7 and a semi-spiracle upper head 9 of the inner cylindrical electrode 4. At the side wall of the upper space 11 of the porous disk 10 is attached an inlet port 12 of the clean carrier gas, which is connected to the outlet of an absolute filter 14 having an air intake 13. An annular slit 15 at the inner wall of the outer cylindrical electrode 4, located at the position facing to the circular bottom end of the semispherical upper head 9, is supply port of the negatively charged ultra-fine particles. The annular slit 15 is surrounded by its annular plenum chamber 15'. The inner cylindrical electrode 4 has at its lower position a circular slit 16 serving as the probe gas extraction port, and it has at its further lower part an extension 17 encasing a counting means of negatively charged ultra-fine particles 18. At a position between the annular slit 15 and the annular covering disk 8 exists an annular porous disk 19 for straightening the upper gas stream. At the side wall of its lower space 20 there exists an outlet port 21 of the carrier gas, which is connected to a suction pump 24 through a gas flow rate meter 22 and a valve 23. The upper part of the inner cylindrical electrode 4 above the slit 16 is supported by a supporting rod 28 which does not disturb the flow of the extracted probe gas from the slit 16 to the lower part of the inner cylindrical electrode 4. The counting means of negatively charged ultra-fine particles 18 is an integral part of the lower part of the inner cylindrical electrode, including: a metal disk-like counter electrode 33, located perpendicular to the cylinder axis and supported by an annular insulator 31, and having a circular mesh portion 32 at its center for allowing passage of the extracted probe gas; a needle-like corona electrode 34 facing perpendicular thereto and insulated therefrom, supported along the cylinder axis with an insulating bushing 35; a variable DC voltage supply 37 connected between the corona electrode 34 and a metal circular disk 36 covering the bottom end of the inner cylindrical electrode 4 and supplying a positive variable DC voltage slightly below the corona onset voltage to the corona electrode 34; a current pulse detector 38 for measuring the burst corona current, connected between the counter electrode 33 and the inner cylindrical electrode and having an independent isolated power supply; an optical fiber 40 transmitting the output pulse signal from the current meter 38 in a form of an optical signal to a pulse counter 39; a concave mirror 43 focusing a light signal from the burst corona occurred at the tip 41 of the corona electrode 34 onto a photo-multiplier tube 42; and a connecting wire 44 for transmitting the output pulse signal from the photo-multiplier tube 42 to the pulse counter 39.

The insulating bushing 35 is supported by a metal partition disk 45, above which there is a gas space 47 having an upper partition out of porous disk 46 for straightening the gas stream in the chamber encasing the corona electrode system and, on its side wall, an outlet port of the extracted probe gas 48 which is connected to a suction pump 51 through a gas flow rate meter 49 and a valve 50.

On the operation of this instrument, the pumps 24 and 51 are started to operate, and their gas suction flow rates are adjusted by the valves 23 and 50 so as to make the flow of the clean carrier gas passing through the gap 52 between the outer and inner cylindrical electrodes 4 and 5 laminar flow path with a gas velocity $v_g$, and so as to make the supply rate of the sample gas with negatively charged ultra-fine particles fed from the slit-like supply port 15 to a sufficiently low level not to disturb the laminar flow of the carrier gas, and so as to make the supply rate of the sample gas equal to the extraction rate of the probe gas from the extraction port 16. Then, the ultra-fine particles imparted with a single negative elementary charge, e [C], and an aerodynamic radius a, that satisfies the Equations (1) and (2) for an applied voltage V, move along a dotted line 53 from the supply port 15 to the extraction port 16 within the electrode gap 52, and they enter into the inside of the lower part 30 of the inner cylindrical electrode 4, pass through the mesh electrode 32 to enter into the corona electrode system, and subject to Coulumbic force to be driven towards the tip 41 of the needle-like corona electrode 34. They enter into the small detecting zone in the close vicinity of the needle tip 41, detach their electrons, and produce the burst coronas, which occur in one-to-one correspondence with the oncoming particles. The concurrent pulse current is detected by the current meter 38 working as the pulse amplifier and fed to the pulse counter 39 through a cable 40. The concurrent light signal is received by the concave mirror 43, focused onto the photo-multiplier tube 42, and fed to the pulse counter 39 through the cable 44. Either one or both of the current and light pulse signals are integrated for a certain period of time. A computer 54 receives the output from the pulse counter 39 through a wire 56 for its integration, and the output from the flow to meter 22, which is proportional to the suction flow rate of the sample gas at the sample gas intake 26, through a wire 57, and also the output of a volt meter 55 for the variable voltage supply 6 through a wire 58. The computer calculate from these variables the absolute number concentration of particles for each particle size, and the size distribution of these particles, both of which are recorded by a data recorder 59.

Figure 2:
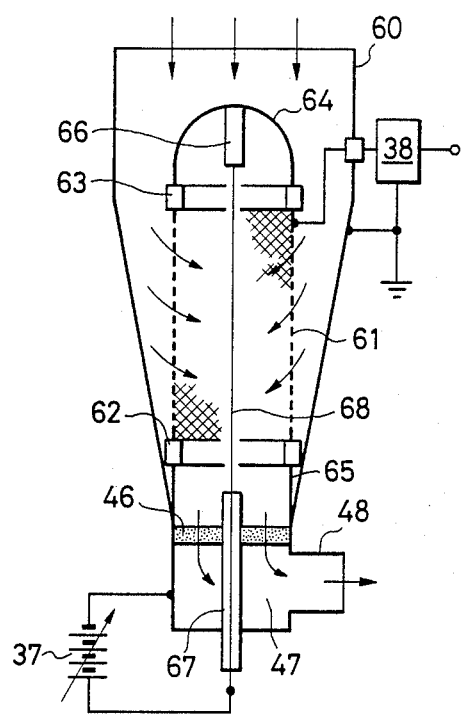
FIGS. 2, 3 and 4 illustrate different modes of embodiment of the measuring means of negatively charged ultra-fine particles used in the present invention.
Figure 3:
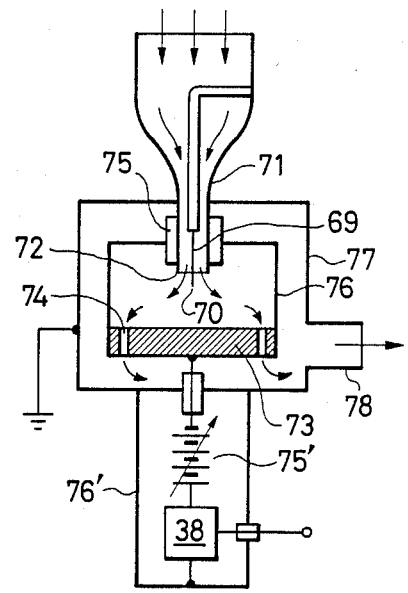
Figure 4:
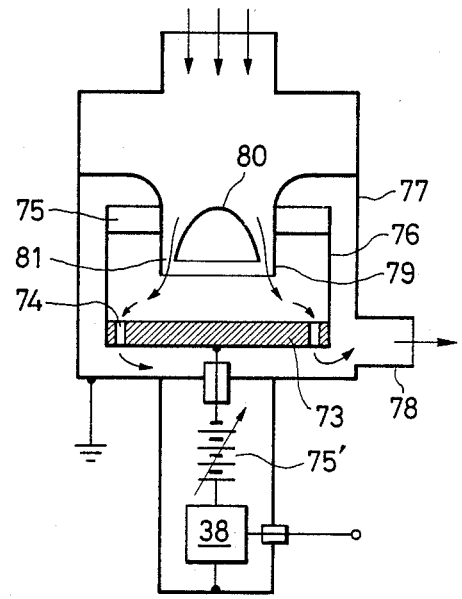

FIGS. 2, 3 and 4, illustrate, respectively, different modes of embodiment of the corona electrode system used for the counting means of negative charged particles 18.

In FIG. 2, the corona electrode system includes a wire corona electrode 68, supported by an insulator 66 and an insulating bushing 67, and a coaxial cylindrical mesh electrode 61 surrounding the wire corona electrode 68 and supported by insulator rings 62 and 63 at its lower and upper ends. The electrode 61 serves as the counter electrode, and has two guard electrodes at its upper and lower ends: one being a semispherical electrode 64 and another a cylindrical electrode 65. The elements 37 through 46 have the same namings and functions as those in FIG. 1. The negatively charged ultra-fine particles enter into the gap between the cylindrical mesh electrode 61 and a conical guide 60 surrounding the electrode 61, and they enter radially into the inter-electrode gap of the corona electrode system through a very large area of the cylindrical mesh counter electrode 61, to reach the long wire corona electrode 68. As a result, a possibility of miscounting, which may be caused by the existence of particles not arriving at the corona electrode owing to the non-symmetric configuration of the corona electrode system, like that in FIG. 1, is greatly reduced.

In FIG. 3, there is a hopper-like coaxial flow guide 71 surrounding the needle-like corona electrode 69, and the extracted probe gas flows through their gap to be fed from the narrow end 72 of the guide 71 directly to the area around the sharp tip 70 of the corona electrode 69. A counter electrode 73 is a disk electrode as the floor of an insulated inner cylindrical chamber 76 which is airtight and supported at its upper center by the gas grounded gap flow guide 71 through an insulating bushing 75, and encased by a coaxial grounded chamber 77. The counter electrode 73 has at its circular periphery a series of outlet ports 74 for discharging the extracted probe gas towards the outlet port 78 of the outer chamber 77. The corona electrode 69 is grounded by being attached to the grounded gas flow guide 71. The insulated counter electrode 73 is supplied with a positive variable DC voltage in relation to the grounded corona electrode 69 from a variable DC voltage supply 75 which is grounded through a pulse current meter 38 for detecting the corona pulse current. This particular type of the corona electrode has an advantage such that the negatively charged ultra-fine particles are fed directly to the detecting zone at the needle tip 70, so that they never undergo the collision by the positive ion cloud produced by the electron avalanche due to the arrival of the leading particle at the tip region and imparts with charge opposite (positive) polarity to be driven to the counter electrode. In other words, the miscounting by such a loss of the particle is greatly reduced, so that this particular type is suitable to the case when a high number concentration of the particles is encountered.

FIG. 4 illustrates the use of a cylindrical knife-edge type corona electrode 79 which is the sharpened edge of a metal cylinder, grounded in this example. There is a coaxial semispherical gas flow guide 80 located in the inside of the cylinder. The extracted probe gap is fed to the circular detecting zone on the circular corona electrode tip 79 through an annular gap 81 between the tip 79 and the lower circular periphery of the flow guide 80. The other elements in this figure have the same naming and function as those in FIG. 3. It is possible to make the diameter of the cylindrical corona electrode 79 much smaller so that it is in a form of the sharp circular edge of a metal pipe.

The advantage of this particular type corona electrode system is that it has the same advantage of reducing the counting loss as that in FIG. 3, and that the particles are fed to the detecting zone through a much broader gap, so that the volumes of both the sample gas and extracted probe gas can be raised.

The present invention enables, by its specific features of construction, a very accurate measurement of number concentration and particle size distribution of ultra-fine particles down to the size range of nanometer or lower, even at a very low particle number concentration.

I claim:

1. A measuring instrument of ultra-fine particles, characterized by comprising a particle precharging means having a gas intake and a gas outlet for imparting negative charge to the ultra-fine particles, a particle separating means consisting of a parallel electrode system with a gas passage in its electric gap and a variable DC voltage supply for applying a variable DC voltage to the electrodes of said parallel electrode system, a carrier gas feed system for feeding clean carrier gas from one end of said parallel electrode system and passing the carrier gas through the gas passage in the electrode gap in a laminar flow to the other end of said parallel electrode system, consisting of a gas intake, absolute filter, and a suction pump, a sample gas feeding means for feeding the sample gas containing the negatively charged ultra-fine particles out of said particle precharging means to the feeding position on the negative electrode of said parallel in electrode system near its upstream end of the carrier gas, consisting of a feed pipe and a sample gas supply port at said feed position, a probe gas suction system for extracting a part of the flow gas together with the arriving negatively charged ultra-fine particles at the extracting position on the positive electrode of said parallel electrode system near its downstream end, consisting of the probe gas extraction port, a gas flow path for passing the extracted probe gas and a suction pump, and a counting means of negatively charged ultra-fine particles located in said gas flow path for detecting and counting said negatively charged ultra-fine particles, which consists of a corona electrode system out of a corona electrode and a counter electrode insulated therefrom, a DC voltage supply for applying a DC voltage between said corona electrode and counter electrode in a polarity so as to make the former electrode positive and a burst corona counter for detecting and counting the light emitted by the burst coronas occuring at the corona electrode.

2. A measuring instrument of ultra-fine particles according to claim 1, characterized by said burst corona counter which consists of a current pulse detector inserted into a circuit comprising said corona electrode system and said variable DC voltage supply and a pulse counter connected to the current pulse detector.

3. A measuring instrument of ultra-fine particles characterized by comprising a particle precharging means having a gas intake and a gas outlet for imparting negative charge to the ultra-fine particles, a particle separating means consisting of a parallel electrode system with a gas passage in its electric gap and a variable DC voltage supply for applying a variable DC voltage to two electrodes of said parallel electrode system, a carrier gas feed system for feeding clean carrier gas from one end of said parallel electrode system and passing the carrier gas through the gas passage in the electrode gap in a laminar flow to the other end of said parallel electrode system consisting of a gas intake, absolute filter and suction pump, a sample gas feeding means for feeding the sample gas containing the negatively charged ultra-fine particles out of said particle precharging means to the feeding position on the negative electrode of said parallel electrode system near its upstream end of the carrier gas consisting of a feed pipe and a sample gas supply port at said feed position, a probe gas suction system for extracting a part of the flow gas together with the arriving negatively charged ultra-fine particles at the extracting position of the positive electrode of said parallel electrode system near its downstream end consisting of a probe gas extraction port, a gas flow path for passing the extracted probe gas and a suction pump, and a counting means of negatively charged ultra-fine particles located in said gas flow path for detecting and counting said negatively charged ultra-fine particles which consist of a corona electrode system out of a corona electrode and a counter electrode insulated therefrom, a DC voltage supply for applying a DC voltage between said corona electrode and counter electrode in a polarity so as to make the former electrode positive and a burst corona counter for detecting and counting the burst coronas occurring at the the corona electrode, the burst corona counter consisting of a photo-detecting means for detecting the light emitted from the burst corona and a pulse counter connected thereto.

* * * * *